(12) United States Patent
Blanz et al.

(10) Patent No.: US 9,194,830 B2
(45) Date of Patent: Nov. 24, 2015

(54) CORRECTION FOR GAIN VARIATION DUE TO FAST CHANGING NMR SENSOR GAIN

(75) Inventors: Martin Blanz, Celle (DE); Thomas Kruspe, Niedersachsen (DE)

(73) Assignee: Baker Hughes Incorporated, Houston, TX (US)

( * ) Notice: Subject to any disclaimer, the term of this patent is extended or adjusted under 35 U.S.C. 154(b) by 896 days.

(21) Appl. No.: 13/412,817

(22) Filed: Mar. 6, 2012

(65) Prior Publication Data

US 2012/0235677 A1   Sep. 20, 2012

Related U.S. Application Data

(60) Provisional application No. 61/453,332, filed on Mar. 16, 2011.

(51) Int. Cl.
*G01R 33/565* (2006.01)
*G01R 33/34* (2006.01)
*G01N 24/08* (2006.01)

(52) U.S. Cl.
CPC .......... *G01N 24/081* (2013.01); *G01R 33/5659* (2013.01)

(58) Field of Classification Search
CPC ... G01V 3/32; G01N 24/081; G01R 33/5659; G01R 33/543; G01R 33/3628; G01R 33/565
USPC ................................................ 324/300–322
See application file for complete search history.

(56) References Cited

U.S. PATENT DOCUMENTS

| | | | |
|---|---|---|---|
| 5,432,446 A * | 7/1995 | MacInnis et al. | 324/303 |
| 6,268,726 B1 * | 7/2001 | Prammer et al. | 324/303 |
| 6,362,619 B2 | 3/2002 | Prammer et al. | |
| 6,448,770 B1 * | 9/2002 | Liu et al. | 324/307 |
| 6,541,969 B2 | 4/2003 | Sigal et al. | |
| 7,026,814 B2 | 4/2006 | Bordon et al. | |
| 7,034,529 B2 | 4/2006 | Blanz et al. | |
| 7,196,516 B2 | 3/2007 | Blanz et al. | |
| 7,358,725 B2 | 4/2008 | Blanz | |
| 7,368,909 B2 | 5/2008 | Blanz et al. | |
| 2002/0167314 A1 * | 11/2002 | Prammer | 324/303 |

OTHER PUBLICATIONS

Notification of Transmittal of the International Search Report and the Written Opinion of the International Searching Authority, or the Declaration; PCT/US2012/029462; Oct. 29, 2012.

(Continued)

*Primary Examiner* — Melissa Koval
*Assistant Examiner* — Rishi Patel
(74) *Attorney, Agent, or Firm* — Cantor Colburn LLP

(57) ABSTRACT

An apparatus for performing nuclear magnetic resonance (NMR) measurements of a material of interest includes an NMR tool and a processor. The NMR tool includes a transmitter antenna; a transmitter coupled to the transmitter antenna; and a receiver antenna configured to receive NMR signals in response to transmitted pulses of electromagnetic energy transmitted by the transmitter antenna. The NMR signals include at least a first signal and a second signal of a phase-alternated group of signals. The processor is configured to receive the NMR signals; receive a first system gain related to the first signal and a second system gain related to the second signal, each system gain being related to a system comprising the NMR tool and the material of interest; and calibrate the NMR signals using the first system gain and the second system gain.

23 Claims, 5 Drawing Sheets

(56) References Cited

OTHER PUBLICATIONS

Sigal, A Method for Enhancing the Vertical Resolution of NMR Logs, Conference Paper, Copyright 2000, Society of Petroleum Engineers Inc., 11 pages, This paper was prepared for presentation at the 2000 SPE Annual Technical Conference and Exhibition held in Dallas, Texas, Oct. 1-4, 2000.

* cited by examiner

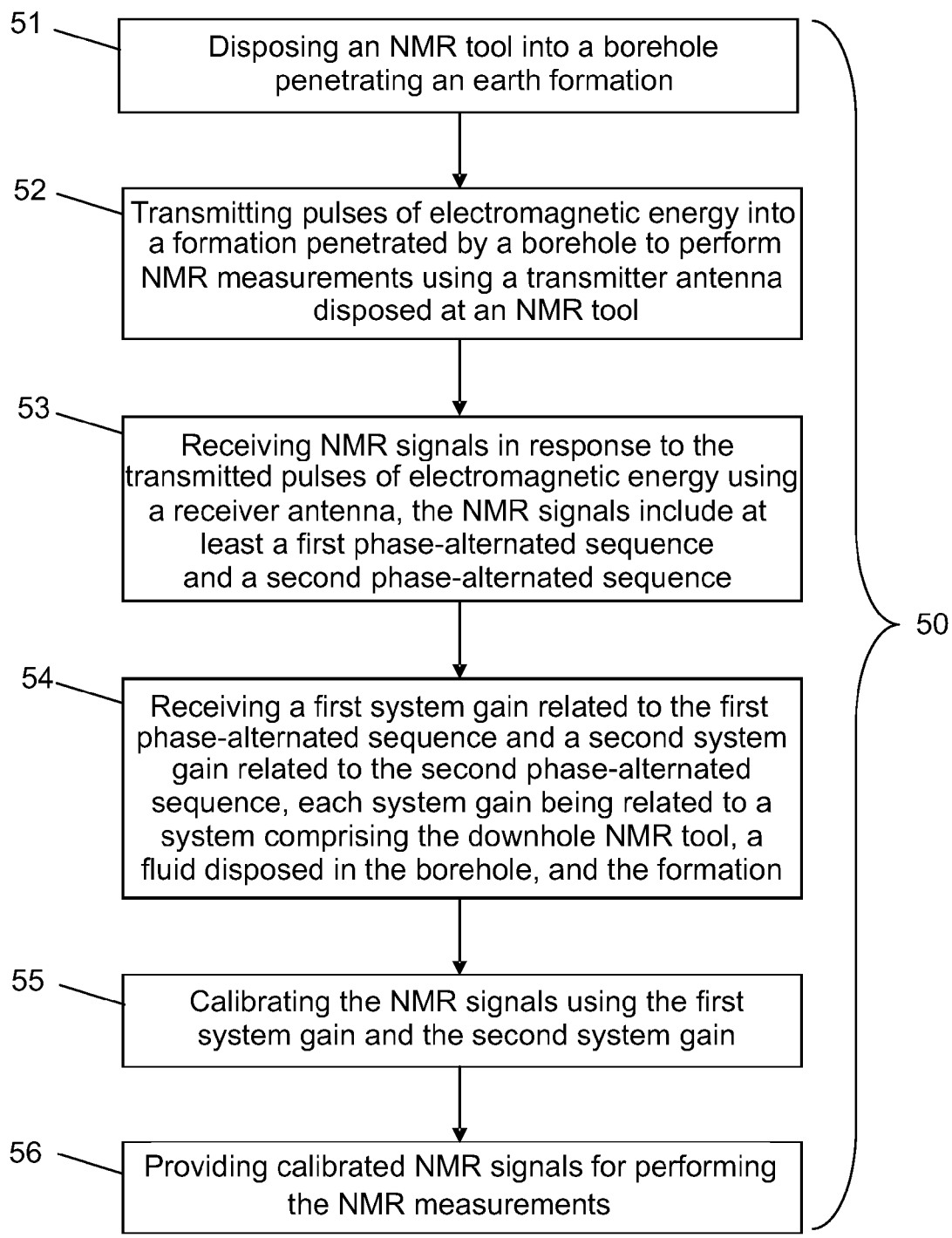

CORRECTION FOR GAIN VARIATION DUE TO FAST CHANGING NMR SENSOR GAIN

CROSS REFERENCE TO RELATED APPLICATIONS

This application claims the benefit of an earlier filing date from U.S. Provisional Application Ser. No. 61/453,332 filed Mar. 16, 2011, the entire disclosure of which is incorporated herein by reference.

BACKGROUND

1. Field of the Invention

The present invention relates generally to determining geological properties of subsurface formations using nuclear magnetic resonance (NMR) measurements for logging boreholes and, particularly, to calibrating apparatus used to perform the measurements.

2. Description of the Related Art

Boreholes are drilled into the earth for many applications such as hydrocarbon production, geothermal production, and carbon dioxide sequestration. In order to efficiently use expensive resources drilling the boreholes, it is important for analysts to acquire detailed information related to the geologic formations being drilled.

Nuclear magnetic resonance (NMR) tools are one type of downhole tool that is particularly useful for performing detailed measurements of properties of hydrocarbon bearing formations. The NMR measurements are used to determine among other things, porosity, hydrocarbon saturation, and permeability of rock formations. The NMR logging tools are used to excite the nuclei of the fluids in the geological formations surrounding the borehole so that certain nuclear spin parameters such as nuclear spin density, longitudinal relaxation time (generally referred to in the art as $T_1$) or transverse relaxation time (generally referred to as $T_2$) of the geological formations can be measured. From such measurements, the porosity, permeability and hydrocarbon saturation are determined, which provides valuable information about the make-up of the geological formations and the amount of extractable hydrocarbons.

A voltage is induced in a receiving coil disposed at the NMR tool by nuclear spins that precess in response to a sequence of magnetic field intensities applied to the nuclei. The induced voltage is typically very small and an amplifier is used to amplify the induced voltage. Because the induced voltage can be very small, various factors can distort and reduce the accuracy of the measurements. These factors include changes in the electrical conductivity of the drilling mud, changes in the electrical conductivity of the formation, and changes in the diameter of the borehole. It would be well received in the drilling industry if the accuracy of NMR measurements could be improved, when borehole and formation parameters may be changing fast.

BRIEF SUMMARY

Disclosed is an apparatus for performing nuclear magnetic resonance (NMR) measurements of a material of interest, the apparatus includes and NMR tool and a processor. The NMR tool includes: a transmitter antenna configured to transmit pulses of electromagnetic energy into the material of interest for performing NMR measurements; a transmitter coupled to the transmitter antenna and configured to generate and control the pulses of electromagnetic energy transmitted by the transmitter antenna; and a receiver antenna disposed at the tool and configured to receive NMR signals in response to the transmitted pulses of electromagnetic energy, the NMR signals include at least a first signal. The processing circuit is configured to: receive the NMR signals; receive a first system gain related to the first signal, the first system gain being related to a system comprising the NMR tool and the material of interest; calibrate the NMR signals using the first system gain; and provide calibrated NMR signals for evaluating the NMR measurements.

Also disclosed is a method for performing nuclear magnetic resonance (NMR) measurements of a material of interest. The method includes transmitting pulses of electromagnetic energy into the material of interest for performing NMR measurements using a transmitter antenna disposed at an NMR tool and receiving NMR signals in response to the transmitted pulses of electromagnetic energy using a receiver antenna, the NMR signals include at least a first signal. The method also includes receiving a first system gain related to the first signal, the first system gain being related to a system comprising the NMR tool and the material of interest and calibrating the NMR signals using the first system gain. The method further includes providing calibrated NMR signals for evaluating the NMR measurements.

Further disclosed is a non-transitory computer-readable medium comprising computer-executable instructions for performing nuclear magnetic resonance (NMR) measurements of a material of interest by implementing a method. The method includes: transmitting pulses of electromagnetic energy into the formation for performing NMR measurements using a transmitter antenna disposed at an NMR tool; receiving NMR signals in response to the transmitted pulses of electromagnetic energy using a receiver antenna, the NMR signals include at least a first signal; receiving a first system gain related to the first signal, the first system gain being related to a system comprising the NMR tool and the material of interest; calibrating the NMR signals using the first system gain; and providing calibrated NMR signals for evaluating the NMR measurements.

BRIEF DESCRIPTION OF THE DRAWINGS

The following descriptions should not be considered limiting in any way. With reference to the accompanying drawings, like elements are numbered alike:

FIG. 5 presents one example of a method for estimating a property of a geologic formation penetrated by the borehole.

DETAILED DESCRIPTION

A detailed description of one or more embodiments of the disclosed apparatus and method presented herein by way of exemplification and not limitation with reference to the Figures.

Disclosed are exemplary embodiments of techniques for calibrating a nuclear magnetic resonance (NMR) downhole tool using correction factors to correct raw or uncalibrated NMR signals. The calibrated signals compensate for various changes in downhole parameters that can affect NMR measurements.

Figure 1:
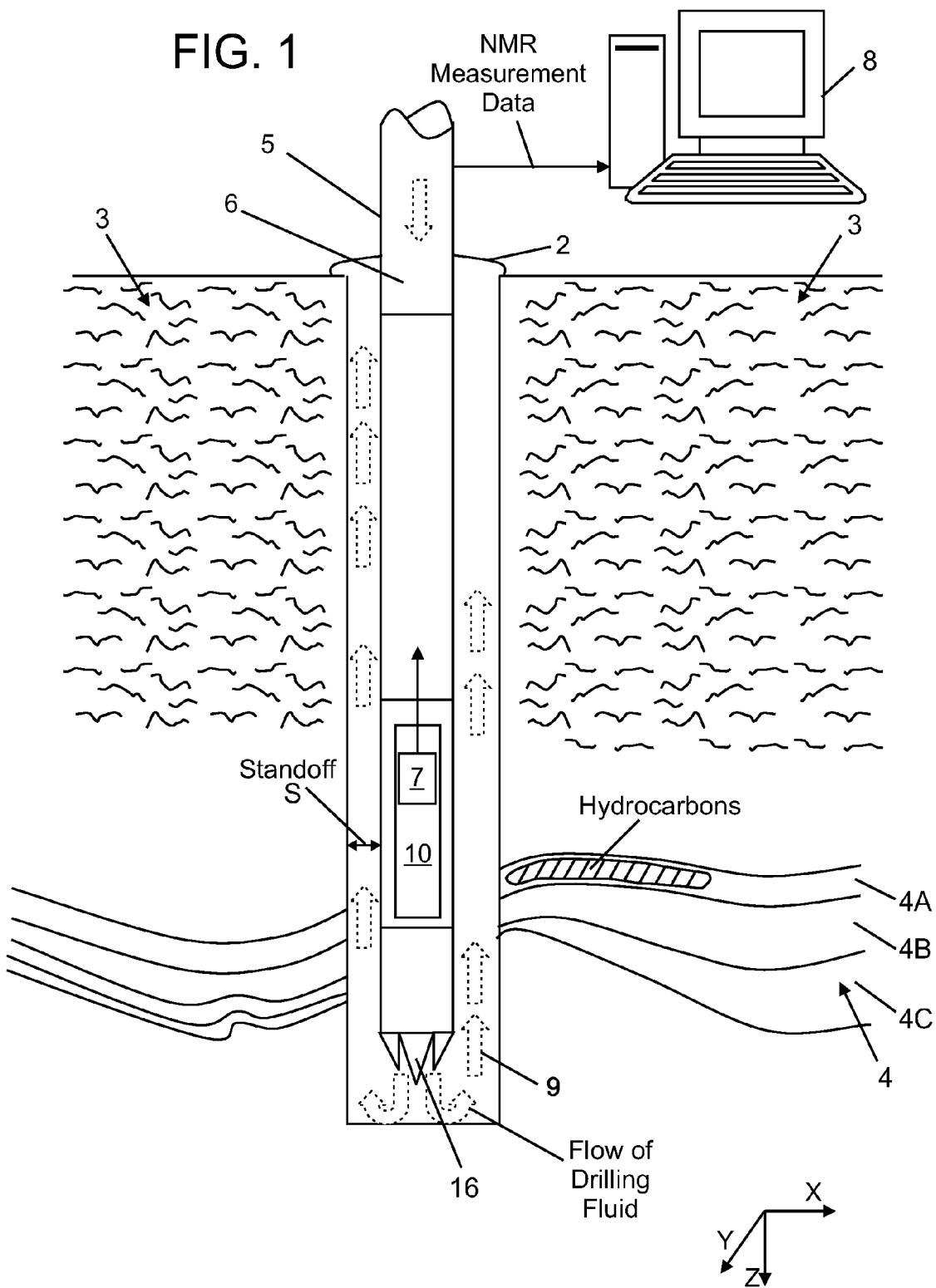
FIG. 1 illustrates an exemplary embodiment of a downhole NMR tool disposed in a borehole penetrating the earth.

FIG. 1 illustrates an exemplary embodiment of a downhole NMR tool 10 disposed in a borehole 2 penetrating the earth 3, which includes an earth formation 4 having layers 4A-4C. The formation 4 represents any subsurface materials of interest upon which NMR measurements may be performed. The downhole tool 10 is conveyed through the borehole 2 by a carrier 5. In the embodiment of FIG. 1, the carrier 5 is a drill string 6. The drill string 6 includes a drill bit 16 for drilling the borehole 2. A drilling rig (not shown) rotates the drill string 6 to drill the borehole 2. A drilling fluid 9 (representing a borehole fluid) is used to lubricate the drill bit 16 and flush cuttings from the borehole 2. The downhole tool is generally spaced a distance S, referred to as standoff, from a wall of the borehole 2. Hence, any signals generated or received by the downhole tool 10 can be affected by the drilling fluid 9 disposed in the standoff.

The downhole NMR tool 10 is configured to perform NMR measurements of properties of the formation 4 while the borehole 2 is being drilled or during a temporary halt in drilling in an application referred to as logging-while-drilling (LWD). In another embodiment, the carrier 5 can be an armored wireline in an application referred to as wireline logging. The wireline is configured to convey the downhole NMR tool 10 through the borehole 2 and provide a communications medium to the surface of the earth 3.

Still referring to FIG. 1, downhole electronics 7 are provided to operate the downhole tool 10 and/or communicate with a surface processing system 8. In LWD applications, a telemetry system (not shown) for communicating with the surface processing system 8 may be provided. Non-limiting embodiments of the telemetry system include pulsed-mud telemetry, wired-drill pipe telemetry, acoustic telemetry, radio telemetry and optical telemetry. Alternatively, NMR measurement data may be stored in the downhole NMR tool 10 and retrieved when the tool 10 is removed from the borehole 2.

Figure 2:
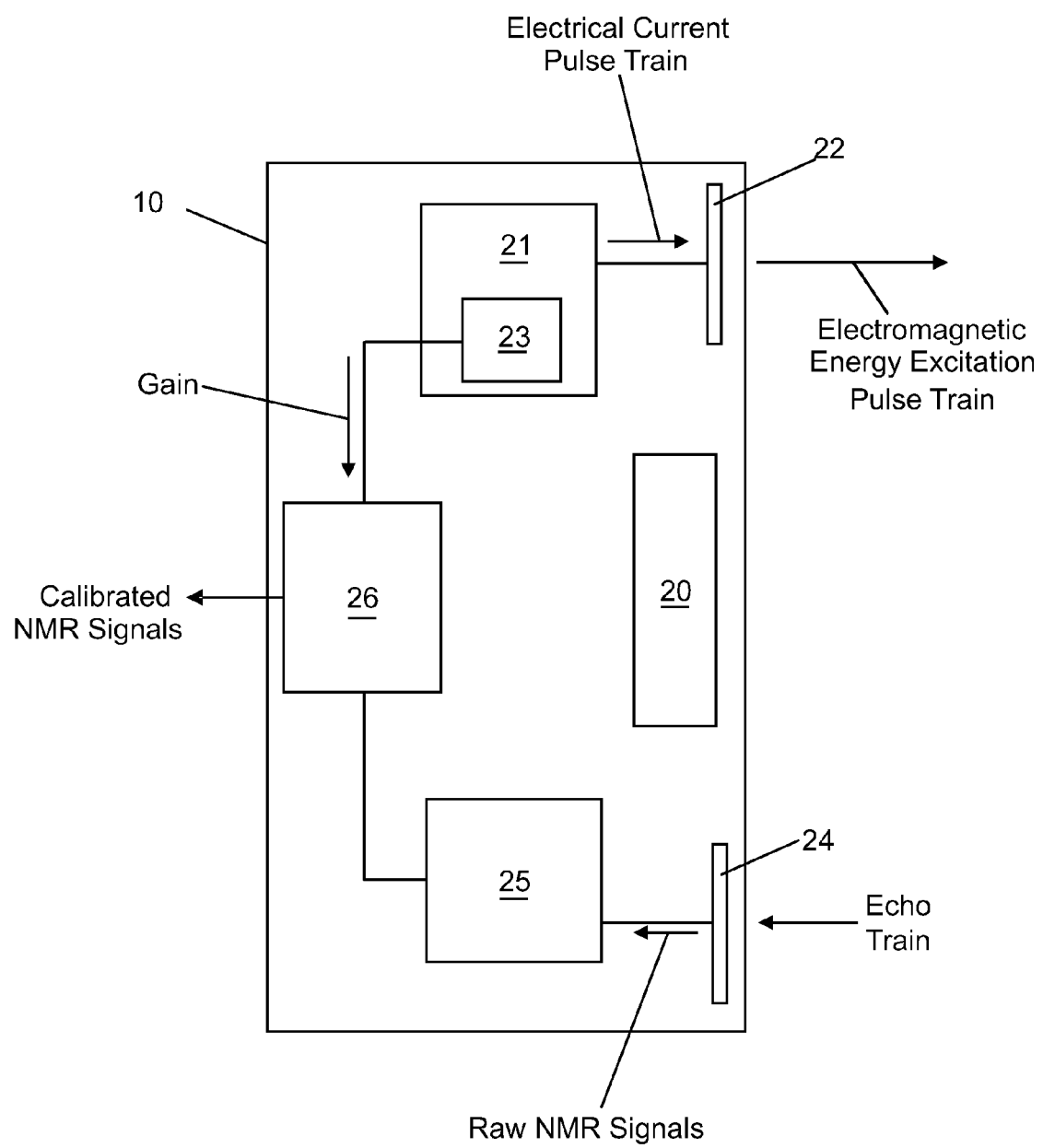
FIG. 2 depicts aspects of the downhole NMR tool.

Reference may now be had to FIG. 2, which depicts aspects of the downhole NMR tool 10 in more detail. The downhole tool 10 includes a magnetic field source 20. The magnetic field source 20 is configured to polarize nuclear spins in a volume of interest (also referred to as a sensitive volume) in the formation 4. A transmitter 21 coupled to a transmitter antenna 22 is configured to transmit radio frequency (RF) pulses of electromagnetic energy to the volume of interest where the pulses interact with the nuclear spins. In one embodiment, the pulses of electromagnetic energy are part of Carr-Purcell-Meiboom-Gill (CPMG) echo trains as known in the art. The transmitter 21 includes a regulator 23 that is configured to regulate the amplitude of pulses of radiofrequency electric current and, thus, regulate the amplitude of the RF pulses emitted by the transmitter antenna 22 into the sensitive volume. As a result of the interaction of the RF pulses with the nuclear spins, the nuclear spins precess at what is known as the Larmor frequency and generate alternating magnetic fields. The alternating magnetic fields known as echoes induce raw NMR signals in a receiver antenna 24. The raw NMR signals are received by a receiver 25 coupled to the receiver antenna 24. A processing circuit 26, which is part of a data acquisition system, is coupled to the transmitter 21 and the receiver 22 and is configured to output calibrated NMR signal measurements of the formation 4 using data from the transmitter 21 and the raw NMR signals. It can be appreciated that in one embodiment one transceiver antenna can be used to perform the functions of both the transmitter antenna 22 and the receiver antenna 24.

The downhole NMR tool 10 may be considered part of an NMR sensor system that includes the borehole fluid 9 and the formation 4 in addition to the tool 10. The system can be described as having an NMR sensor system gain. The NMR sensor system gain is dependent on several factors. For instance, the NMR sensor system gain is proportional to the quality factor Q of the NMR receiver antenna 24, which in turn is dependent on the quality factor Q of the transmitter antenna 22. In addition, the quality factors of the antennas are dependent on the damping of those antennas. The damping is caused by the electrical conductivity of the borehole fluid 9, the electrical conductivity of the formation 4, and other causes.

The downhole NMR tool 10 is generally calibrated frequently during operation in the borehole 2. In one embodiment, calibration includes applying correction factors to the raw NMR signals obtained during measurements. For recalibration of the raw NMR signals, the NMR sensor gain is measured by injecting a known electrical signal into an NMR sensor resonator and measuring the response in the data acquisition system. In one embodiment, this gain measurement is performed about once per minute and the measured gain is then used for all the NMR measurement re-calibrations/corrections until the next gain measurement is performed.

A raw NMR signal consists of the wanted or true NMR signal+ringing+offset. Ringing and offset are non-NMR signals not related to nuclei in the sensitive volume. The term "ringing" relates to an unwanted system response while the term "offset" relates to an unwanted deviation from a true signal. Radio-frequency pulses typically cause ringing after each pulse due to magneto-acoustic or electronic effects for example. Ringing can be very large and tend to overwhelm the true NMR signal from the nuclei. To isolate the true NMR signal, the ringing and offset must be removed. This is done by phase cycling. By phase cycling, so-called phase alternate pairs (PAPs) of NMR echo sequences are generated. That is, two NMR signals having opposite phases are obtained for an NMR measurement in the sensitive volume. In a PAP sequence, two echo trains are acquired as a result of the RF pulses. The phase of an alternate excitation pulse is inverted and causes a phase inversion of all the resulting echoes. The term "excitation pulse" relates to a first pulse of a pulse train or sequence.

Figure 3A:
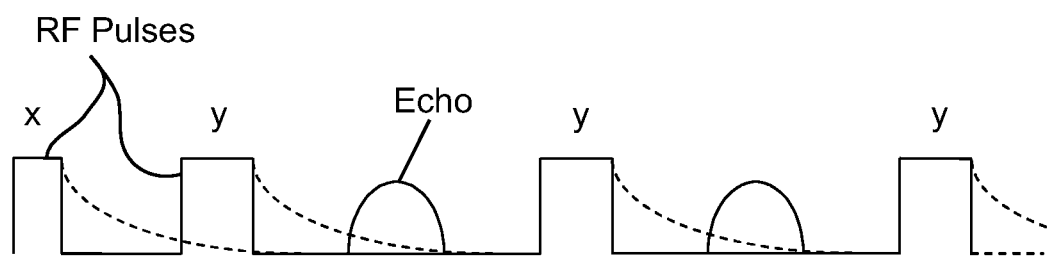
FIGS. 3A and 3B, collectively referred to as FIG. 3, depict aspects of a phase-alternated pair of sequences for acquired NMR signals.
Figure 3B:
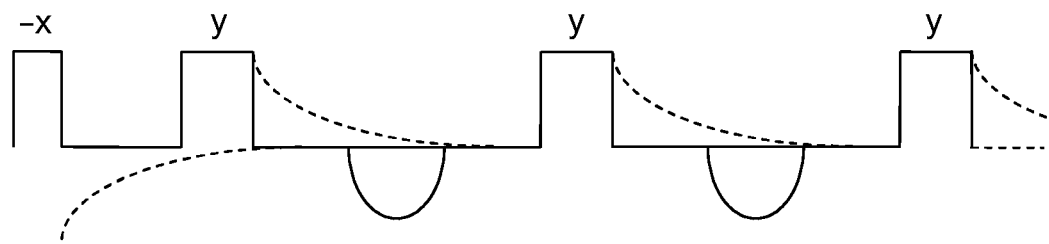

FIG. 3 illustrates a phase-alternated pair of sequences, showing RF pulses, echoes and ringing (dashed lines). Offset is zero in FIG. 3. FIG. 3A represents sequence 1 of the PAP while FIG. 3B represents sequence 2 of the PAP. The phases of the RF pulses are labeled x, y, −x or −y to denote phases of 0°, 90°, 180° or 270°, respectively. Therefore, the RF pulse sequence of FIG. 3A can be written as x y y y . . . and that of FIG. 3B as −x y y y . . . .

In general, each of the offset and the ringing may be in part proportional to the receiving antenna gain and in part independent of the antennal gain, depending on how the offset and the ringing are caused. The acquired uncalibrated raw NMR signals of a PAP can be represented as:

$$A1 = g \cdot NMR + (g+a) \cdot R + (g+b) \cdot O \text{ and}$$

$$A2 = -g \cdot NMR + (g+a) \cdot R + (g+b) \cdot O$$

where A1 and A2 are the acquired signals, NMR is the wanted NMR signal, "g" is the antenna gain, and "a" and "b" are fixed factors for ringing R and offset O, respectively.

Hence, by subtraction of one sequence of the acquired signals from the other sequence of the acquired signals of a PAP, ringing and offset can be canceled resulting in a doubling of the wanted NMR signal:

$$A1-A2=2g \cdot \text{NMR}.$$

Thus, the correctly calibrated NMR signal can be obtained by dividing the difference of the acquired NMR signals by twice the previously measured gain (i.e., by 2·g):

$$\text{NMR}=(A1-A2)/2g.$$

It is noted that because of equal gains g in both sequences of the PAP, it is of no consequence that offset and ringing are composed of gain-dependent and fixed parts.

There may be situations when the NMR sensor system gain may vary so fast that the above method of straight subtraction of the one part from the other of a PAP and recalibrating with a common gain can lead to inaccurate results. The fast gain variation may be caused by a fast borehole diameter change (such as caused by washouts) or by a fast change of the electrical conductivity of formation or mud. The latter may be caused by a variable concentration or size of gas bubbles in the mud during underbalanced drilling, for example.

In order to overcome the problem of fast gain variations of the NMR sensor system gain, an NMR sensor system gain determination concurrent with the NMR measurement is disclosed along with a different mathematical treatment of the PAPs. These techniques are now explained in detail below.

In one embodiment, continuous regulation of the transmit current is employed to keep the transmitted NMR radio-frequency (RF) pulses at the required amplitude. The output of the regulator 23, as shown in FIG. 2, to control the RF pulse current is dependent on the NMR sensor system damping. Hence, by observing the output of the regulator, the NMR transmitting antenna Q can be obtained at least approximately. Normally, the NMR receiving antenna gain will be proportional to this Q. In other words, the NMR sensor system gain is a function of the regulator output. The regulator output may, for example, be a voltage, a current, a pulse width, a mark space ratio, or a numerical value (of a digital regulator). As the actual NMR sensor system gain can be obtained at any time, the NMR signal can be re-calibrated at any time. The acquired uncalibrated raw NMR signals need to be obtained in phase alternated echo sequences and then re-calibrated.

Re-calibration of NMR signals having phase alternated echo sequences (sequence 1 and sequence 2) with different gains (g1 for sequence 1 and g2 for sequence 2) is now discussed. The PAP signals with different gains may be written as:

$$A1=g1 \cdot \text{NMR}+(g1+a) \cdot R+(g1+b) \cdot O \text{ and} \qquad (1)$$

$$A2=-g2 \cdot \text{NMR}+(g2+a) \cdot R+(g2+b) \cdot O. \qquad (2)$$

NMR, R, O, a and b are unknown variables. With two equations and five unknowns, various cases are provided to be able to solve these equations.

In a first case, ringing and offset are not gain dependent. Equations (1) and (2) above can then be simplified as:

$$A1=g1 \cdot \text{NMR}+R+O \text{ and} \qquad (3)$$

$$A2=-g2 \cdot \text{NMR}+R+O. \qquad (4)$$

Subtracting these two equations yields:

$$A1-A2=(g1+g2) \cdot \text{NMR}. \qquad (5)$$

The correctly calibrated NMR signal is obtained by dividing the difference of the acquired NMR signals by the sum of the two gains:

$$\text{NMR}=(A1-A2)/(g1+g2). \qquad (6)$$

Unfortunately, ringing is generally gain dependent and equation (6) may not be used frequently.

In a second case, ringing and offset are gain dependent, but have no fixed contribution to the acquired NMR signals. In this case, equations (1) and (2) can be simplified as:

$$A1=g1 \cdot \text{NMR}+g1 \cdot (R+0) \text{ and} \qquad (7)$$

$$A2=-g2 \cdot MR+g2 \cdot (R+0). \qquad (8)$$

The acquired signals A1 and A2 are then divided by their gains:

$$A1/g1=\text{NMR}+(R+O) \text{ and} \qquad (9)$$

$$A2/g2=-\text{NMR}+(R+O). \qquad (10)$$

Subtracting equation (10) from equation (9) yields:

$$\text{NMR} = \frac{A1}{2 \cdot g1} - \frac{A2}{2 \cdot g2}. \qquad (11)$$

Ringing is generally gain-dependent and equation (11) may be used frequently. It is noted that in state of the art receivers the offset is generally negligible and, thus, equation (11) may also be used for this case.

The phase-alternated pair equations (1) and (2) can be expanded to represent a phase-alternated quadruplet (PAQ) of sequences, which is shown in FIG. 4. FIG. 4 shows RF pulses, echoes, and ringing (dashed lines). FIGS. 4A, 4B, 4C and 4D represent sequences 1, 2, 3 and 4, respectively. If only three of the sequences are used, then this would be referred to as a phase-alternated triplet (PAT). The PAQ acquired signals can be represented as:

$$A1=g1 \cdot \text{NMR}+(g1+a) \cdot R+(g1+b) \cdot O \qquad (12)$$

$$A2=-g2 \cdot \text{NMR}+(g2+a) \cdot R+(g2+b) \cdot O \qquad (13)$$

$$A3=g3 \cdot \text{NMR}-(g3+a) \cdot R+(g3+b) \cdot O \qquad (14)$$

$$A4=-g4 \cdot \text{NMR}-(g4+a) \cdot R+(g4+b) \cdot O. \qquad (15)$$

An equivalent form of equations (12)-(15) is:

$$A1=g1 \cdot \text{NMR}+g1 \cdot R+g1 \cdot O+a \cdot R+b \cdot O \qquad (16)$$

$$A2=-g2 \cdot \text{NMR}+g2 \cdot R+g2 \cdot O+a \cdot R+b \cdot O \qquad (17)$$

$$A3=g3 \cdot \text{NMR}-g3 \cdot R+g3 \cdot O-a \cdot R+b \cdot O \qquad (18)$$

$$A4=-g4 \cdot \text{NMR}-g4 \cdot R+g4 \cdot O-a \cdot R+b \cdot O. \qquad (19)$$

It is noted that there are four equations, but still five unknown variables and parameters. If one of the "unknown" parameters is known a priori, e.g., to be negligible, then the system of equations is solvable. Commercially available math programs can be used to solve this (non-linear) system of equations. Two examples of using these equations are now presented.

In one example, the offset has no gain-dependent part and equations (16)-(19) become:

$$A1=g1 \cdot \text{NMR}+g1 \cdot R+a \cdot R+O \qquad (20)$$

$$A2=-g2 \cdot \text{NMR}+g2 \cdot R+a \cdot R+O \qquad (21)$$

$$A3=g3 \cdot \text{NMR}-g3 \cdot R \cdot a \cdot R+O \qquad (22)$$

$$A4 = -g4 \cdot NMR - g4 \cdot R - a \cdot R + O. \quad (23)$$

Note that O in equations (20)-(23) represents b·O of equations (16)-(19).

Equations (20)-(23) can be solved yielding the following result:

$$NMR = \frac{(g1-g2)\cdot(A3-A4)+(g3-g4)\cdot(A1-A2)}{2\cdot(g1\cdot g3 - g2\cdot g4)}. \quad (24)$$

Figure 4A:
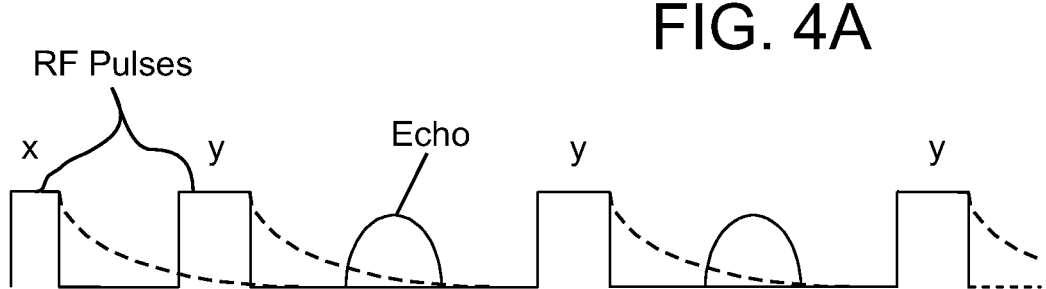
FIGS. 4A-4D, collectively referred to as FIG. 4, depict aspects of a phase-alternated quadruplet of sequences for acquired NMR signals.
Figure 4B:
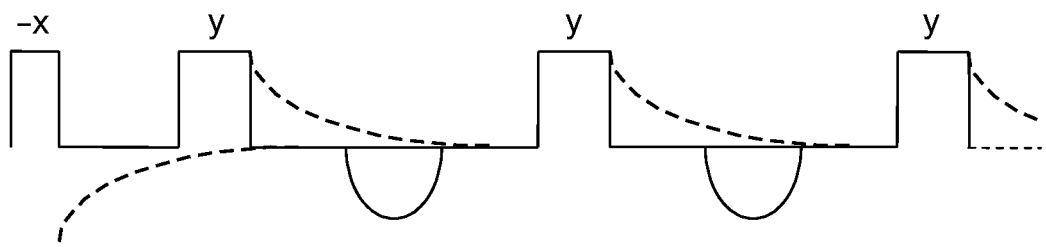
Figure 4C:
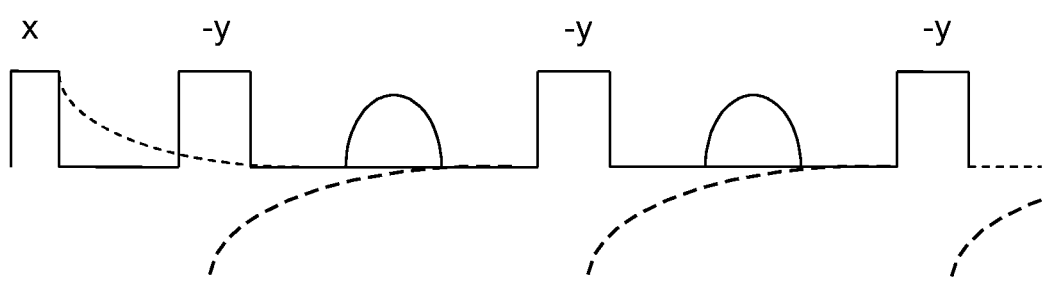
Figure 4D:
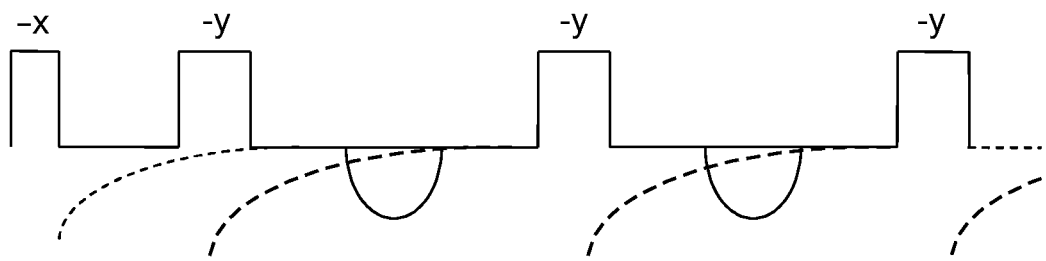

In another example, the offset has no gain-dependent part, but the ringing is gain-dependent. With this example, only the first three sequences (i.e., PAT) shown in FIGS. 4A-4C are needed and are represented as follows:

$$A1 = g1 \cdot NMR + g1 \cdot R + O \quad (25)$$

$$A2 = -g2 \cdot NMR + g2 \cdot R + O \quad (26)$$

$$A3 = g3 \cdot NMR - g3 \cdot R + O. \quad (27)$$

Equations (25)-(27) can be solved to determine the wanted NMR signal:

$$NMR = \frac{g1\cdot(A3-A2)+g2\cdot(A1-A3)+g3\cdot(A1-A2)}{2\cdot g1\cdot(g2+g3)}. \quad (28)$$

Equation (28) works well to eliminate gain-dependent ringing and gain-independent offset.

In one embodiment, depending on how fast the quality factor Q of the receiver antenna varies, it may be sufficient to determine an average NMR sensor gain for a whole echo sequence but different for each sequence of a PAP, PAT or PAQ.

In one embodiment, if the quality factor Q of the receiver antenna varies very fast, an individual gain for each individual echo needs to be determined as opposed to one gain used for an entire half of a PAP echo train. Hence, when the two acquired NMR echo sequences of a PAP are subtracted from each other, the previously determined individual gains for each echo need to be used. In this case, the above equations are meant for two corresponding echoes of the two halves of a PAP and not for whole echo trains. When each echo is calibrated, a train (i.e., an array) of gains is obtained that correspond with a train of echoes for each half of a PAP echo train. The procedure just described is for a PAP, but PAT and PAQ can be treated alike.

Separating ringing and offset can be useful for diagnostic purposes. In principle, each set of acquired echo sequence data may consist of three systematic signals (i.e., the NMR signal, the offset, and the ringing) and random noise. The treatment of the signals above concentrated on eliminating offset and ringing to get the undistorted NMR signal. Similarly, it is possible to solve the equations describing the acquired NMR signals for the unknowns other than NMR to get the ringing and/or the offset of the NMR tool for diagnostic purposes.

NMR signals are complex signals having in-phase and quadrature components as are ringing and offset. For simplicity of discussion, this was not explicitly accounted for in the above calculations. Nevertheless, the above equations can be used independently for the in-phase and quadrature parts of the signals.

FIG. 5 presents one example of a method 50 (use of a phase-alternated pair (PAP) of sequences) for performing nuclear magnetic resonance (NMR) measurements of a formation penetrated by a borehole. The method 50 calls for (step 51) disposing an NMR tool in the borehole. Further, the method 50 calls for (step 52) transmitting pulses of electromagnetic energy into the formation for performing NMR measurements using a transmitter antenna disposed at the NMR tool. Further, the method 50 calls for (step 53) receiving NMR signals in response to the transmitted pulses of electromagnetic energy using a receiver antenna. The NMR signals are derived from a first and a second sequence of a pair of phase-alternated sequences. Further, the method 50 calls for (step 54) receiving a first system gain related to the first sequence and a second system gain related to the second sequence of the pair of phase alternated sequences. Each system gain being related to a system comprising the downhole NMR tool, a fluid disposed in the borehole, and the formation. Further, the method 50 calls for (step 55) calibrating the NMR signals using the first system gain and the second system gain. Further, the method 50 calls for (step 56) providing calibrated NMR signals for evaluating the NMR measurements. Evaluating may include determining a property of the formation or formation fluid using the calibrated NMR signals.

The phase-alternated triplet or quadruplet sequence (illustrated in FIG. 4) can also be used to advantage to characterize ringing of the NMR tool. If the echo signals of FIG. 4C are subtracted from the echo signals of FIG. 4A, then the offset and NMR signal are subtracted and the only signal remaining is the ringdown or ringing. For diagnostic purposes (e.g., in a workshop), it is very useful to characterize ringing by separating it from the offset and the NMR signal.

It should be emphasized that all pulse and echo phases, illustrated in the figures, Are phases relative to each other. For example, if starting in absolute terms in FIG. 3A with a y phase excitation pulse, then the following refocus pulses would need to be −x and the echoes would all be shifted by 90° with respect to the original sequence. In addition, it should be emphasized that the sign of phase changes may be reversed. For example, the pulses of the pair of sequences of FIG. 3 have phases x y y y ... and −x y y y .... Using the pair of sequences x −y −y −y ... and −x −y −y −y ... will also generate NMR echoes. Similar variations are possible with respect to the sequences of possible with respect to the sequence of FIG. 4.

A further family of NMR echo sequences that can be used in practicing the teachings disclosed herein is the group of sequences with phase alternating refocus pulses as described in U.S. Pat. No. 7,034,529 B2. One RF pulse sequence in this group is x x −x x −x x ... (illustrated in FIG. 4 in said U.S. patent) that may be combined with −x x −x x −x x ... (illustrated in FIG. 5 in said U.S. patent) to remove offset and ringing.

It should be noted that the terms "train" and "sequence" are used synonymously, i.e., echo train or echo sequence has the same meaning. It should also be noted that the term "signal" may relate to a single echo or a sequence of echoes. To be clear, a first signal may include a single echo or a sequence of echoes and, correspondingly, a second signal can include a single echo or a sequence of echoes. Accordingly, a gain related to a signal may relate to a whole echo sequence that may have a common gain or that every echo may have an individual gain. Further, it should be noted that single NMR echoes can be acquired by using just two pulses without generating a sequence or train of echoes.

In support of the teachings herein, various analysis components may be used, including digital and/or analog circuitry. For example, the downhole electronics 7, the surface processing system 8, the transmitter 21, the regulator 23 or the processing circuit 26 may include digital and/or analog circuitry. The circuits may include components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first," "second," "third," and "fourth" are used to distinguish elements and are not used to denote a particular order. The term "couple" relates to a first component being coupled to a second component either directly or indirectly through an intermediate component.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for performing nuclear magnetic resonance (NMR) measurements of a material of interest, the apparatus comprising:
   an NMR tool comprising:
      a transmitter antenna configured to transmit pulses of electromagnetic energy into the material of interest for performing NMR measurements;
      a transmitter coupled to the transmitter antenna and configured to generate and control the pulses of electromagnetic energy transmitted by the transmitter antenna;
      a receiver antenna disposed at the tool and configured to receive NMR signals in response to the transmitted pulses of electromagnetic energy, the NMR signals include at least a first signal; and
   a processing circuit configured to:
      receive the NMR signals;
      receive a first system gain related to the first signal the first system gain being related to a system comprising the NMR tool and the material of interest;
      calibrate the NMR signals using the first system gain; and
      provide calibrated NMR signals for evaluating the NMR measurements;
   wherein:
      the NMR signals further include a second signal, the first signal and the second signal being of a phase-alternated group of signals; and
      the processing unit is further configured (i) to receive a second system gain related to the second signal of the phase-alternated group of signals, the second system gain being related to the system comprising the NMR tool and the material of interest, and (ii) to calibrate the NMR signals using the second system gain.

2. The apparatus according to claim 1, wherein one single antenna comprises the transmitter antenna and the receiver antenna.

3. The apparatus according to claim 1, wherein the calibrated NMR signals correct for at least one of ringing and offset.

4. The apparatus according to claim 1, wherein the first signal and the second signal each comprise NMR and non-NMR signals where the NMR signal of the second signal has a phase opposite of the corresponding NMR signal of the first signal.

5. The apparatus according to claim 4, wherein the received NMR signals further include a third signal having a phase opposite the phase of the first or second signal.

6. The apparatus according to claim 5, wherein the received NMR signals further include a fourth signal having a phase opposite the phase of the third signal.

7. The apparatus according to claim 4, wherein the processor is further configured to remove at least one of ringing and offset by solving the following equation:

$$NMR = \frac{A1}{2 \cdot g1} - \frac{A2}{2 \cdot g2}$$

where NMR is the calibrated NMR signal, A1 is the first signal, A2 is the second signal, g1 is the first system gain, and g2 is the second system gain.

8. The apparatus according to claim 7, wherein the first signal comprises a first train of NMR echoes and the second signal comprises a second train of NMR echoes.

9. The apparatus according to claim 8, wherein the first signal comprises a NMR echo of the first echo train and the second signal comprises a corresponding NMR echo of the second echo train.

10. The apparatus according to claim 9, wherein the first gain comprises a first train of gains associated with acquiring the first train of NMR echoes in the first signal and the second gain comprises a second train of gains associated with acquiring the second train of NMR echoes in the second signal.

11. The apparatus according to claim 10, wherein the processor is further configured to provide the calibrated NMR signals for the first train of NMR echoes and the second train of NMR echoes using the first train of gains and the second train of gains.

12. The apparatus according to claim 1, wherein the transmitter comprises a regulator configured to regulate the pulses of electromagnetic energy transmitted by the transmitter antenna to maintain a selected amplitude.

13. The apparatus according to claim 12, wherein electric current sent to the transmitter antenna is regulated.

14. The apparatus according to claim 13, wherein the regulator is coupled to the processing circuit and is configured to send a gain signal comprising the gain to the processing circuit.

15. The apparatus according to claim 1, wherein the material of interest comprises a formation penetrated by a borehole, the NMR tool is a downhole NMR tool configured to be conveyed through the borehole, and the system comprises the downhole NMR tool, a fluid disposed in the borehole, and the formation.

16. The apparatus according to claim 15, wherein the NMR tool is conveyed through the borehole by a wireline or a drill string.

17. A method for performing nuclear magnetic resonance (NMR) measurements of a material of interest, the method comprising:
transmitting pulses of electromagnetic energy into the material of interest for performing NMR measurements using a transmitter antenna disposed at an NMR tool;
receiving NMR signals in response to the transmitted pulses of electromagnetic energy using a receiver antenna, the NMR signals include at least a first signal;
receiving a first system gain related to the first signal, the first system gain being related to a system comprising the NMR tool and the material of interest;
calibrating the NMR signals using the first system gain; and
providing calibrated NMR signals for evaluating the NMR measurements;
wherein:
the NMR signals further include a second signal, the first signal and the second signal being of a phase-alternated group of signals, and the receiving NMR signals includes receiving the second signal;
the receiving a first system gain related to the first signal includes receiving a second system gain related to the second signal of the phase alternated group of signals, the second system gain being related to the system comprising the NMR tool and the material of interest; and
the calibrating NMR signals includes using the second system gain.

18. The method according to claim 17, wherein the first signal and the second signal each comprise NMR and non-NMR signals where the NMR signal of the second signal has a phase opposite of the corresponding NMR signal of the first signal.

19. The method according to claim 18, further comprising separating the first signal and the second signal into in-phase and quadrature-phase parts.

20. The method according to claim 17, wherein the first system gain and the second system gain are received from a regulator configured to regulate the output of a transmitter coupled to the transmitter antenna.

21. The method according to claim 17, further comprising determining a ringing or an offset or combination thereof of the NMR tool.

22. The method according to claim 17, wherein the material of interest comprises a formation penetrated by a borehole, the NMR tool is a downhole NMR tool configured to be conveyed through the borehole, and the system comprises the downhole NMR tool, a fluid disposed in the borehole, and the formation and the method further comprises disposing the downhole NMR tool in the borehole.

23. A non-transitory computer-readable medium comprising computer-executable instructions for performing nuclear magnetic resonance (NMR) measurements of a material of interest by implementing a method comprising:
transmitting pulses of electromagnetic energy into the formation for performing NMR measurements using a transmitter antenna disposed at an NMR tool;
receiving NMR signals in response to the transmitted pulses of electromagnetic energy using a receiver antenna, the NMR signals include at least a first signal;
receiving a first system gain related to the first signal the first system gain being related to a system comprising the NMR tool and the material of interest;
calibrating the NMR signals using the first system gain; and
providing calibrated NMR signals for evaluating the NMR measurements
wherein:
the NMR signals further include a second signal, the first signal and the second signal being of a phase-alternated group of signals, and the receiving NMR signals includes receiving the second signal;
the receiving a first system gain related to the first signal includes receiving a second system gain related to the second signal of the phase alternated group of signals, the second system gain being related to the system comprising the NMR tool and the material of interest; and
the calibrating NMR signals includes using the second system gain.

* * * * *